United States Patent [19]

McIntosh

[11] Patent Number: 4,815,446
[45] Date of Patent: Mar. 28, 1989

[54] PROCESS FOR TREATING METASTASIS OF CANCEROUS TUMORS

[75] Inventor: Norma L. McIntosh, Whittier, Calif.

[73] Assignee: Alpha Therapeutic Corporation, Los Angeles, Calif.

[21] Appl. No.: 732,841

[22] Filed: May 9, 1985

[51] Int. Cl.[4] .............................................. A61B 19/00
[52] U.S. Cl. .......................................... 600/3; 128/1.1
[58] Field of Search ................... 128/1 R, 1.1, 1.2, 653

[56] References Cited

U.S. PATENT DOCUMENTS 4,434,788 3/1984 Nakatsugawa ....................... 128/1.1

FOREIGN PATENT DOCUMENTS 83304632.9 8/1983 European Pat. Off. .

OTHER PUBLICATIONS

"Perfluorochemical Possibly Applies to Brain Tumor Therapy", Mitsuyama et al., 1982, Nygoya Health University.
"Radiation Sensitization of Artificial Blood Substitute (Fluosol-DA)", Hishikawa-Itro et al., (Summarized Translation by N. Washio) 1983.
"Use of Perfluorochemical Emulsions to Improve Oxygenation in Solid Tumors", Rockwell et al., Yale University, 1983.
"Experimental Studies on the Possible Combined Chemotherapy to Neoplasms with Fluosol-DA Infusion", Ohyanagi et al., 1983, Advances in Blood Substitute Research, pp. 315-320.
"Synergistic Effect of Perfluorochemicals on BCNU Chemotherapy-Experimental Study in a 9L Rat Brain-Tumor Model", Kuwamura et al., Kobe Univ., Japan.
"Increased Efficacy of Radiotherapy in Mice Treated with Perfluorochemical Emulsions Plus Oxygen," B. Teicher and S. Rockwell (Abstracted from 1983 American Association of Cancer Research Meeting, May 25-28).
"Perfluorocarbon Emulsions in Cancer Therapy: Preliminary Observations on Presently Available Formulations," Robert L. Goodman, M.D., Robert E. Moore, Ph.D., Mary E. Davis, B.S., David Stokes, B.S., and John M. Yuhas, Ph.D.
European Patent Application Ser. No. 83304632.9 to R. E. Moore Published Apr. 18, 1974 (Publication No. 0 105 584).
"Enhancement of Anticancer Drug Efficacy by a Perfluorocarbon Emulsion (PFC)," B. A. Teicher and C. M. Rose (Abstracted from 1984 American Association of Cancer Research Meeting).
"Perfluorochemical Emulsions Can Increase Tumor Radiosensitivity," B. A. Teicher and C. M. Rose, Science, vol. 223, Mar. 2, 1984.
"Macrophages and Cancer Metastasis," I. J. Fidler and G. Poste.
"Metastasis: Tracking the Seeds of Cancer," K. White, Medical World News, Dec. 26, 1983.
"Ultrastructure of Tumoricidal Peritoneal Exudate Cells Stimulated In Vitro by Perfluorochemical Emulsions," M. L. Miller, J. D. Stinnett and L. C. Clark, Jr., J. Reticuloendothelial Soc., vol. 27, No. 2, Feb. 1980.

Primary Examiner—Kyle L. Howell
Assistant Examiner—Randy Citrin
Attorney, Agent, or Firm—Christie, Parker & Hale

[57] ABSTRACT

A method of controlling metastasis of a cancerous tumor in a patient is disclosed. The method comprises administering a perfluorocarbon compound (PFC) emulsion to the patient at intervals of from about 3 to 14 days during a treatment period. PFC emulsion is administered initially in an amount of from about 2 to about 15 milliliters per kilogram of patient body weight. Subsequently administration of PFC emulsion do not exceed about 15 milliliters per kilogram of body weight. Oxygen is administered daily for at least three days following each administration of PFC emulsion & preferably every day during the treatment period. Radiation and/or chemothereapeutic agents may be administered to the patient in conjunction with the administration of PFC emulsion and oxygen.

37 Claims, 4 Drawing Sheets

Days Post Fluosol-DA Administration

PROCESS FOR TREATING METASTASIS OF CANCEROUS TUMORS

FIELD OF THE INVENTION

The present invention relates to cancer therapy and in particular to the infusion of oxygen carrying perfluorocarbon compound emulsions into cancer patients to stimulate macrophage activity to thereby reduce metastasis and augment treatment of primary cancerous tumors.

BACKGROUND OF THE INVENTION

One of the greatest problems in the treatment of cancerous tumors is metastasis, i.e., the transmission of cells of the primary tumor to other locations in the patient and the establishment of new tumors at such locations. Metastasis is difficult to control because it often occurs before the primary tumor is diagnosed and treated. Also, the metastatic lesions may be locations which limit the effective dosages of the treatments, e.g., radiation, due to the sensitivity of the surrounding tissue to such treatments. Further, metastatic cells are heterogeneous and cells which are resistant to conventional therapy tend to emerge.

Conventional methods for treating metastasis include surgery, radiotherapy and/or chemotherapy. Other approaches which have been proposed include the use of monoclonal antibodies, hyperthermia, radiation sensitizing and protective drugs, and stimulated macrophages.

It has been reported that Fidler et al in "Macrophages and Cancer Metastasis" that macrophages can be stimulated to become tumoricidal. Tumoricidal macrophages have the ability to discriminate between metastatic or tumorigenic and normal cells. Thus, although tumor cells are heterogeneous, they are all susceptible to lysis by the activated macrophages.

Two pathways to achieve macrophage activation in vivo are disclosed. One pathway involves macrophage interaction with microorganisms or their products such as endotovins, the bacteria wall skeleton and small components of the bacteria cell wall, e.g., muramyl dipeptide. Another pathway for activating macrophages involves the interaction of macrophages with soluble mediators released by sensitized lymphocytes, e.g., soluble lymphokine.

Each of the above pathways has drawbacks. For example, water soluble synthetic muramyl dipeptide tends to be rapidly excreted by the body and therefore renders the macrophages tumoridical for only a brief period. Lymphokine only activates the macrophages for three to four days after which the macrophages are resistant to reactivation. In animals it has been found that many of the drawbacks surrounding the activation of macrophages by lymphokine can be overcome by encapsulating the lymphokine within liposome.

SUMMARY OF THE INVENTION

Applicant's invention is based on the discovery that macrophage activity can be stimulated to reduce metastasis of cancerous tumors by the administration to the patient of an aqueous perfluorocarbon compound (PFC) emulsion and by administration of oxygen to the patient for a select number of days following PFC emulsion administration.

Accordingly, there is provided a method for reducing metastasis of a cancerous tumor in a patient which comprises administering to the patient an aqueous PFC emulsion in an amount of from about 2 to about 15 milliliters of PFC emulsion and preferably of from about 4 to about 10 milliliters of emulsion per kilogram of body weight of the patient. Oxygen, preferably hyperbaric oxygen (up to 3 ATM) high-inspired oxygen or carbogen is administered to the patient for a period of at least about 15 minutes and preferably for from about one to about four hours per day for at least about three days following PFC emulsion administration, i.e., the day of PFC emulsion administration and the next two days thereafter, and preferably at least five days following PFC emulsion administration.

Preferably, the PFC emulsion is administered to the patient at intervals of from about 3 to about 14 days during a predetermined treatment period. In such an embodiment, the PFC emulsion is initially administered in an amount of from about 2 to about 15 milliliters of PFC emulsion per kilogram of body weight of the patient. Subsequent administrations preferably do not exceed about 15 milliliters and more preferably do not exceed about 10 milliliters of PFC emulsion per kilogram of patient body weight per week during the treatment period. Oxygen is administered to the patient daily for at least three days following each PFC emulsion administration and preferably every day during the treatment period.

Applicant has further found that such increased macrophage activity significantly enhances the effectiveness of radiotherapy and chemotherapy processes on primary tumor growth. Accordingly, there is provided a method for reducing the growth of cancerous tumors and for controlling metastasis of such tumors which comprises administering PFC emulsion, oxygen and radiation to the patient. The PFC emulsion is administered to the patient at least once and preferably at selected intervals of from about 3 to about 14 days during a treatment period. The PFC emulsion is administered initially in an amount of from about 2 to about 15 and preferably from about 6 to about 15 milliliters of PFC emulsion per kilogram of patient body weight. Subsequent administrations of PFC preferably do not exceed about 15 milliliters and more preferably do not exceed about 10 milliliters of PFC emulsion per kilogram of body weight per week.

Oxygen is administered to the patient for a period of at least about 15 minutes and preferably of from about one to four hours for at least three days following the administration of PFC emulsion and preferably every day for the entire treatment period.

A predetermined dosage of radiation, preferably in the range of from about 1,000 to about 8,000 rads, is administered to the patient following administration of the PFC emulsion and oxygen. Preferably oxygen is administered immediately prior to and during irradiation. In a particularly preferred embodiment of the invention, the radiation is administered in fractionated doses over the treatment period at predetermined intervals. Each such fractionated dose is preferably in the range of from about 100 to about 600 rads and the interval of radiation treatment is between 1 and 10 times per week for a period of between 2 and 8 weeks.

In another particularly preferred embodiment of the invention, there is provided a method for treating primary cancerous tumors and metastasis which comprises administration of a PFC emulsion oxygen and a chemotherapeutic agent. The PFC emulsion is administered at least once and preferably at first predetermined intervals of from about 3 to about 21 days during a treatment period.

The PFC emulsion is administered initially in an amount of from about 2 to about 15 and preferably of from about 4 to about 10 milliliters of PFC emulsion per kilogram of body weight. Subsequent administrations preferably do not exceed about 15 milliliters and more preferably do not exceed about 10 milliliters of PFC emulsion per kilogram of body weight per week.

The chemotherapeutic agent is administered to the patient at second predetermined intervals of from about 1 to about 28 days, depending on the particular chemotherapeutic agent which is administered. The chemotherapeutic agent is preferably administered sequentially with, simultaneously with, or more preferably as a mixture with the PFC emulsion.

Oxygen is administered to the patient for a period of at least about 15 minutes and preferably from about 1 to about 4 hours after each day for at least about three days following each administration of the PFC emulsion and for at least about 2 to about 5 days following administration of the chemotherapeutic agent. More preferably, oxygen is administered on a daily basis throughout the treatment period.

In a particularly preferred embodiment of the invention, PFC emulsion administration is combined with the administration of radiation and at least one chemotherapy agent. The method comprises administering an aqueous PFC emulsion of the patient at least once and preferably at first predetermined intervals of from about 3 to about 14 days during a treatment period. The PFC emulsion is administered initially in an amount of from about 2 to about 15 milliliters and preferably from about 6 to about 10 milliliters of PFC emulsion per kilogram of body weight. Subsequent administrations of PFC emulsion do not exceed about 15 milliliters and preferably do not exceed about 10 milliliters of PFC emulsion per kilogram of body weight per week. Oxygen is administered to the patient for at least about 15 minutes and preferably from about 1 hour to about 4 hours for at least three days following the administration of the PFC emulsion and preferably daily throughout the treatment period.

A chemotherapeutic agent is administered to the patient at least once and preferably at second predetermined intervals of from about 1 to about 28 days, depending on the particular chemotherapeutic agent used. The chemotherapeutic agent is administered sequentially with, simultaneously with, or more preferably as a mixture with PFC emulsion.

Radiation is also administered to the patient preferably in an amount of from about 1,000 to about 8,000 rads. The radiation is preferably fractionated and administered at third predetermined intervals over the treatment period.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION

Figure 1:
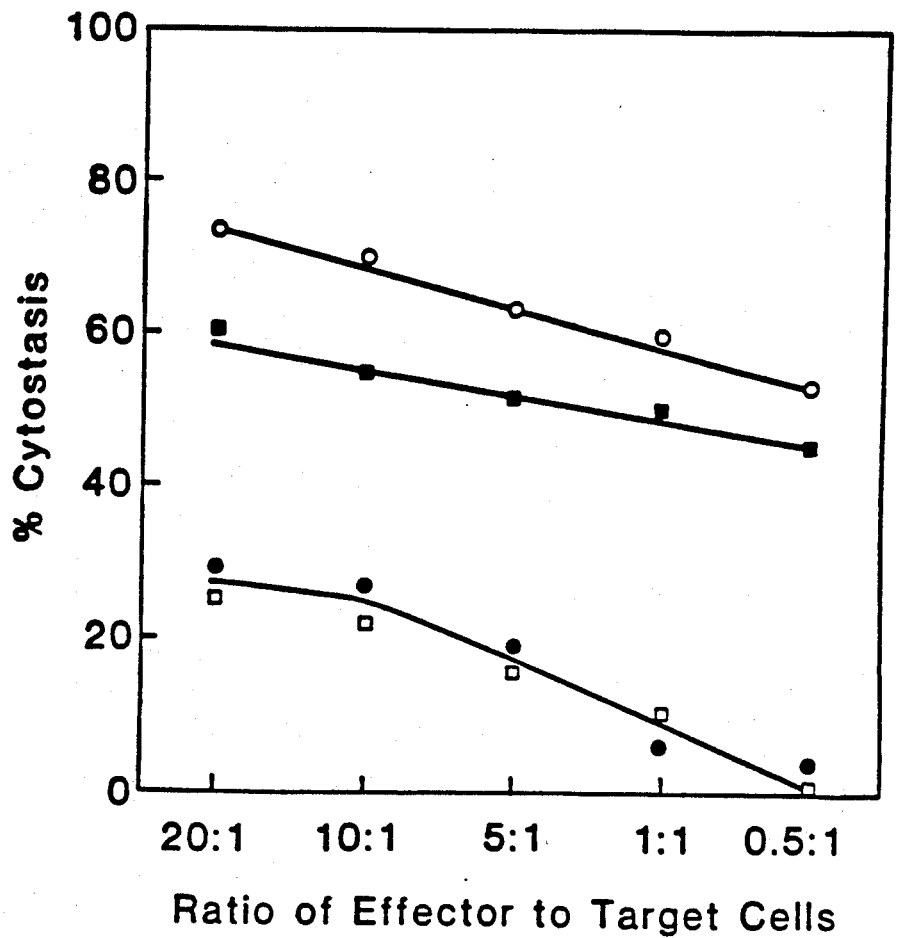
FIG. 1 is a graph showing Percentage Cytostastis vs. Ratio of Effector to Target Cells resulting from the experiments described in Example II herein.

In accordance with the present invention, there is provided a method for stimulating macrophage tumoricidal activity to reduce metastasis of a cancerous tumor. The method comprises administering a perfluorocarbon compound emulsion to the patient at least once and preferably two or more times at select intervals during a predetermined treatment period. The intervals are preferably from about 3 to about 14 days, although intervals of up to about 21 days may be used in certain cases.

Oxygen is administered daily for a period of at least about three days after each administration of PFC emulsion during the treatment period and preferably every day during the treatment period.

The initial administration of PFC emulsion is in an amount of from about 2 to about 15 and preferably from about 4 to about 10 milliliters of PFC emulsion per kilogram of patient body weight. Such amounts provide a fluorocrit, i.e., volume of perfluorocarbon material following centrifugation of whole blood, as measured within one hour of administration, in the range of from about 0.4% to about 3.0% and preferably of from about 0.8% to about 2.0% respectively.

The amounts of PFC emulsion described herein are expressed in milliliters of PFC emulsion containing about 20 grams of perfluorocarbon compound per 100 milliliters of emulsion ("20% wt./vol."). It is to be understood that emulsions containing more or less perfluorocarbon compound may be used in which case the indicated volumes should be increased proportionately for emulsions containing less than 20% perfluorocarbon compound and decreased proportionately for emulsions containing more than 20% perfluorocarbon compound emulsion.

Initial administration of PFC emulsion in amounts greater than about 15 milliliters per kilogram of patient body weight are not preferred because such amounts had to diminish the enhancement of the macrophage activity rather than stimulating such activity. It is believed that amounts greater than about 15 milliliters per kilogram of body weight overstimulate the macrophages rendering them less active than normal and indeed may be lethel to the macrophages.

Amounts of PFC emulsion less than about 2 milliliters per kilogram of patient body weight are not preferred because no beneficial stimulating effect is seen by the administration of such amounts of PFC emulsion. It is believed that such amounts are too small to significantly stimulate the macrophages.

Amounts of PFC emulsion within the range of from about 4 to about 10 milliliters per kilogram of patient body weight are believed to provide the optimum combination of macrophage stimulation with minimal harm to the macrophages.

Subsequent administration of PFC emulsion are in amounts which should not exceed about 15 milliliters and preferably do not exceed about 10 milliliters of PFC emulsion per kilogram of patient body weight per week during the treatment period. Subsequent administrations of PFC emulsions in amounts greater than about 15 milliliters per kilogram of patient body weight per week are not preferred because it has been found that such amounts tend to diminish the activity of the macrophages. It is believed that subsequent administrations of PFC emulsions in amounts greater than about 15 milliliters per kilogram of patient body weight per week overstimulate and/or kill the macrophages.

As used herein, "perfluorocarbon compound emulsion" refers to an aqueous emulsion of an oxygen-transferable perfluorocarbon compound, preferably having a particle size of less than about 0.3 microns. Suitable emulsions have good oxygen transferability to ischemic, hypoxic and anoxic tissues, a favorable vapor pressure range to allow reasonable expiration of the perfluorocarbon compounds used in the emulsion and clinically acceptable toxicity, the emulsion may be transparent, translucent or opaque.

The perfluorocarbon compound emulsion comprises at least one perfluorocarbon compound, an emulsifier and physiological salts and monoglycerides thereof. Such perfluorocarbon compound emulsions are described in U.S. Pat. Nos. 3,911,138 to Clark, Jr., 3,962,439 to Yokoyama et al, and 4,252,827 to Yokoyama et al, Yokoyama, K. et al: "A Perfluorochemical Emulsion as an Oxygen Carrier", *Artificial Organs* 8: 34–40, 1984, and Yokoyama, D. et al: "Selection of 53 PFC Substances for Better Stability of Emulsion and Improved Artificial Blood Substances", *Advances in Blood Substitute Research,* New York: Liss, Inc., 1983, Reiss, J. G.: "Reassessment of Criteria for the Selection of Perfluorochemicals for Second-Generation Blood Substitutes: Analysis of Structure/Property Relationships", *Artificial Organs,* 8: 44–56, 1984, all of which are incorporated herein by reference.

Preferred fluorocarbon compound emulsions comprise at least one perfluorocarbon compound having 9-11 carbon atoms selected from the group consisting of perfluorodecalin, perfluoromethyldecalin, perfluoro alkylcyclohexanes having 3 to 5 carbon atoms in the alkyl, perfluoro alkyltetrahydrofurans having 5 to 7 carbon atoms in the alkyl, perfluoro alkyltetrahydropyrans having 4 to 6 carbon atoms in the alkyl, perfluoroalkanes having 9 to 11 carbon atoms; and may have at least one perfluoro tert-amine having 9 to 11 carbon atoms selected from the group consisting of perfluoro tert-alkylamines having 9 to 11 carbon atoms, perfluoro N-alkylpiperidines having 4 to 6 carbon atoms in the alkyl and perfluoro N-alkylmorpholines having 5 to 7 carbon atoms in the alkyl. Such emulsions further comprise high-molecular-weight nonionic surfactant having a molecular weight of about 2,000 to 20,000; a phospholipid; and at least one fatty acid compound selected from the group consisting of fatty acids having 8 to 22 carbon atoms; and physiologically acceptable salts and monoglycerides thereof. The ratio of the the perfluorocarbon compound and the said perfluorotert-amine is 95-50 to 5-50 by weight.

The "high-molecular-weight nonionic surfactant" has a molecular weight of 2,000 to 20,000 and includes polyoxyethylene-polyoxypropylene copolymers, polyoxyethylene alkyl ethers, and polyoxyethylene alkyl aryl ethers. The concentration of the surfactant in the emulsion is about 2.0 to about 5.0%, preferably 3.0 to 3.5% (W/V).

The symbol "% (W/V)" means the amount proportion of a material by weight (gram) based on 100 ml of the resulting emulsion.

Examples of the perfluorocarbons having 9 to 11 carbon atoms are a perfluorocycloalkane or perfluoro alkylcycloalkane which includes, for example, perfluoro $C_{3-5}$-alkylcyclohexanes such as perfluoromethylpropylcyclohexane, perfluorobutylcyclohexane, perfluorotrimethylcyclohexane, perfluoroethylpropylcyclohexane, perfluorodecalin and perfluoromethyldecalin; a perfluoro $C_{4-6}$-alkyltetrahydropyran such as perfluorohexyltetrahydropyran; a perfluoro $C_{5-7}$-alkyltetrahydrofuran such as perfluoro pentyltetrahydrofuran, perfluoro hexyltetrahydrofuran and perfluoro heptyltetrahydrofuran; and a perfluoroalkane having 9–11 carbon atoms such as perfluorononane and perfluorodecane.

Examples of the perfluoro tert-amine having 9 to 11 carbon atoms are a perfluoro tert-alkylamine having 9 to 11 carbon atoms which includes, for example, perfluorotrialkylamines such as perfluoro N,N-dibutylmonomethylamine, perfluoro N,N-diethylpentylamine, perfluoro N,N-diethylhexylamine, perfluoto N,N-dipropylbutylamine and perfluorotripropylamine; a perfluoro N,N-dialkylcyclohexylamine having 9-11 carbon atoms such as perfluoro N,N-diethylcyclohexylamine; a perfluoro N-$C_{4-6}$-alkylpiperidine such as perfluoro N-pentylpiperidine, perfluoro N-hexylpiperidine and perfluoro N-butylpiperidine; and a perfluoro N-$C_{5-7}$-alkylmorpholine such as perfluoro N-pentylmorpholine, perfluoro N-hexylmorpholine and perfluoro N-heptylmorpholine.

The ratio of the perfluorocarbon compound to the perfluoro tert-amine to be used is 50-95 to 50-5 by weight and the total amount of perfluorocarbon compound and perfluoro tert-amine contained in the emulsion is about 10 to about 50% (W/V).

The phospholipids used as emulsifier adjuvant in the invention are ones commonly used in the art, and those comprising yolk phospholipid or soybean phospholipid are preferable. The amount present in the emulsion ranges from about 0.1 to about 1.0% (W/V), and preferably about 0.4 to about 0.6% (W/V).

The fatty acid compound used as emulsifying adjuvant is a fatty acid having 8 to 22 carbon atoms, a physiologically acceptable salt such as sodium or potassium salt or a monoglyceride thereof, which includes, for example, caprylic acid, capric acid, lauric acid, myristic acid, palmitic acid, stearic acid, behenic acid, palmitoleic acid, oleic acid, linoleic acid, arachidonic acid and sodium or potassium salt and monoglyceride thereof. These fatty acid compounds may be used alone or as a mixture of two or more kinds thereof in such a minor amount of 0.004 to 0.1% (W/V), and preferably about 0.02 to 0.04% (W/V). Among these fatty acid compounds, the preferable ones are those having 14 to 20 carbon atoms and their physiologically acceptable salts, and the most preferable are potassium palmitate and potassium oleate, taking into consideration of their good solubility and ease of the preparation of the emulsion.

The presently preferred perfluorocarbon compound emulsion is manufactured by the Green Cross Corporation of Osaka, Japan and sold under the trade name Fluosol-DA. The specifics of the nature and composition of Fluosol-DA including the formulation thereof is described and claimed in U.S. Pat. No. 4,252,827. Fluosol is a registered U.S. trademark of the Green Cross Corporation of Osaka, Japan.

The perfluorocarbon compound emulsion may be oxygenated prior to administration to the patient by known techniques. If pre-oxygenated, the indicated partial pressure of oxygen in the PFC emulsion is preferably about 300 to 650 millimeters of mercury.

Following each administration of PFC emulsion, oxygen is administered to the patient daily for at least about three days including the PFC treatment day. Preferably oxygen is administered every day during the treatment period. The oxygen is preferably administered as hyperbaric oxygen at pressures of up to about three atmospheres, carbogen (95% oxygen, 5% carbon dioxide) or high-inspired oxygen (50% to 100% oxygen) to allow the lungs to saturate the perfluorocarbon compound emulsion with oxygen while in systemic circulation. Administration of the oxygen is performed by having the patient breathe the oxygen for a period of at least about 15 minutes and preferably from about one to about four hours.

In addition to controlling the spread of cancer by metastasis, the present invention is particularly useful in combination with radiotherapy and/or chemotherapy in controlling the growth of primary metastatic cancerous tumors. In a preferred method, administration of PFC emulsion and oxygen is combined with the administration of radiation.

In the process, PFC emulsion is administered to the patient at least once and preferably at intervals of from about 3 to about 14 days during the treatment period. The amount of PFC emulsion which is initially administered is preferably in the range of from about 6 to about 15 milliliters of PFC emulsion per kilogram of patient body weight and subsequent administrations are in amounts which do not exceed about 15 milliliters and preferably do not exceed about 10 milliliters of PFC emulsion per kilogram of patient body weight per week during the treatment period.

It is preferred that the PFC emulsion be administered initially in an amount of at least about 6 milliliters per kilogram of patient body weight because such an amount is believed to be required to effectively oxygenate hypoxic areas of the primary tumor. Such oxygenation sensitizes the tumor to radiation thereby enhancing the effect of the radiotherapy. Amounts of PFC emulsion greater than about 15 milliliters are again not preferred because such amounts tend to diminish the enhancement of the macrophage activity.

Again, oxygen is administered to the patient daily for at least three days following each administration of PFC emulsion and preferably every day during the treatment period. Each administration of oxygen is preferably performed by breathing hyperbaric oxygen, carbogen or high inspired oxygen for a period of at least about 15 minutes and preferably from about one to about four hours.

Radiation is administered to the patient at the location of the tumor, following administration of oxygen to the patient and preferably within three days following administration of PFC emulsion. The radiation is preferably administered in fractionated doses.

The indicated dosage of radiation, number of doses and of the details of the radiation treatment program are selected according to the treatment which is normally prescribed for the type of tumor being treated and likewise for its stage of development and location. In conventional tumor radiation therapy, several radiation fractionation schedules, e.g., 100–600 rads/fraction in programs calling for a total dose of 1,000–8,000 rads are currently clinically used. Typically, such fractional doses of radiation are administered to the patient at intervals of one to ten times a week over a period of two to eight weeks. A presently preferred radiation program calls for the administration of radiation in doses of about 140 to about 240 rads five times a week for a period of about six to about eight weeks.

To assure that the hypoxic areas of the tumor are oxygenated during the administration of radiation, oxygen is preferably administered to the patient for 30 to 120 minutes prior to exposure to X-ray or gamma ray irradiation. Pre-oxygenation of the PFC emulsion prior to administration is also preferred. During radiation treatment, it is preferred that the patient continue to breathe oxygen and continue such oxygen breathing for 0 to about 60 minutes or more following radiation treatment.

The radiation is preferably administered to the patient externally, however, alternative forms of radiation therapy can be utilized including intraoperative radiation procedures which consist of single or multiple radiation treatment of high dosages (1,000–2,500 rads) and implant radiation using a variety of radiation sources. Implant radiation consists of a continuous radiation source. In such an embodiment of the invention, the schedule of administration of oxygen and PFC administration is designed to maximize the macrophage stimulation and tumor-growth-delay effect in conjunction with the duration and half-life of the radiation source implanted. The sources of radiotherapy that may be used include X-rays, gamma rays, neutron, irridium, radium and cesium radiation.

The addition of the combination of PFC and oxygen according to the foregoing techniques is believed to result in significant sensitizing of the tumor to radiotherapy.

In another preferred embodiment of the invention, one or more chemotherapeutic agents are administered in addition to the PFC emulsion and oxygen. In such a method, the PFC emulsion is again administered at least once and preferably at intervals of from about 3 to about 21 days during the treatment period. The amount of PFC emulsion administered to the patient is again initially in an amount of from about 2 to about 15 and preferably of from about 4 to about 10 milliliters of PFC emulsion per kilogram of patient body weight. Subsequent administrations of PFC emulsions preferably do not exceed 15 and preferably do not exceed 10 milliliters per kilogram of patient body weight per week.

Again, oxygen is administered to the patient as described above on a daily basis for at least three days following each administration of PFC emulsion and preferably every day during the treatment period.

The chemotherapeutic agent is administered to the patient at least once and preferably at selected intervals, e.g., from 1 to 28 days, during the treatment period. The amount of the chemotherapeutic agent, the number of administrations, the intervals between administrations as well as other details of the chemotherapy treatment program are selected according to the treatment which is normally prescribed for the specific chemotherapeutic agent which is used, the type of tumor being treated and its stage of development and location.

Some chemotherapeutic agents or drugs are known to be oxygen dependent, e.g., the presence of oxygen may be required for or may at least enhance the transport of the chemotherapeutic agent across the tumor cell membrane, may enhance cell cycliing, and/or may enhance the toxicity or specificity of the chemotherapeutic agent toward tumor cells. Examples of oxygen dependent chemotherapeutic agents include methotrexate, vinblastine, vincristine, cyclophosphamide and daunomycin, VP-16 and BCNU.

Other chemotherapeutic agents are known which are not oxygen dependent. This includes androgens, estrogens, anti-estrogen, progestins, adrenal steroids, nitrogen mustard, cyclophosphamide, thio-TEPA, busulfan, 6-mercaptopurine, 6-thioguanine, 5-fluorouracil, cytosine arabinoside, adriamycin, dactinomycin, daunomycin, bleomycin, mithramycin, mitomycin-C, CCNU, methyl-CCNU, DTIC, hydroxyurea, cis-platinum (cis-platinum (II) diamminedichloride), procarbazine, mexamethylmelamine, L-asparaginase, and the like. Lipophilic drugs such as alkylating agents as well as macrophage activity factors such as lymphokines may also be used.

The chemotherapeutic drugs may be administered simultaneously with PFC emulsion, as a mixture with PFC emulsion or at intervals which are independent of the administration of the PFC emulsion. It is presently preferred that the chemotherapeutic agent be administered simultaneously with the administration of PFC emulsion and more preferably as a mixture with the PFC emulsion.

It is believed that simultaneous administration and particularly administration of the chemotherapeutic agent as a mixture promotes delivery of the chemotherapeutic agent to the tumor via macrophage transport. It is believed that a chemotherapeutic agent dissolved in the PFC emulsion will be engulfed by macrophages which will then carry the chemotherapeutic agent to the tumor and the activity of the chemotherapeutic agent may be enhanced by the oxygen-carrying capacity of the PFC laden macrophage which may further stimulate the tumoricidal effect of the macrophage.

When an independent administration schedule is used, the PFC emulsion is preferably administered at intervals which assure oxygenated PFC in systemic circulation at the time that the chemotherapeutic agent is administered to enhance the transport of the chemotherapeutic agent to the tumor and, if oxygen dependent, to enhance the effectiveness of the chemotherapeutic agent.

In a particularly preferred embodiment of the invention macrophage stimulation according to the present invention is combined with radiotherapy and chemotherapy to treat primary cancerous tumors and to control metastasis. In such a process, the intervals at which radiation and chemotherapeutic agents are administered, the dosages of radiation and chemotherapeutic agent given at each such intervals as well as other details of the radiation and chemotherapy treatment are selected based upon conventional schedules normally prescribed for the tumor being treated.

The PFC emulsion and oxygen are administered in amounts and at intervals as described above which stimulate the macrophages, enhance the transport of the chemotherapeutic agent to the tumor via macrophage transport, enhance the tumoricidal effect of oxygen dependent chemotherapeutic agents and oxygenate hypoxic cells in the tumor to increase the sensitivity of those cells to radiation and cytotoxicity. Accordingly, the PFC emulsion is administered at least once and preferably at intervals of from about 3 to about 21 days and preferably from 3 to about 14 days during the treatment period. Oxygen is administered as described above for at least 3 days following PFC emulsion administration and preferably every day during the treatment period.

The amount of PFC emulsion in the initial administration is preferably at least 2 milliliters per kilogram of patient body weight to stimulate macrophage activity and more preferably at least 6 milliliters per kilogram of patient body weight to provide sufficient PFC to oxygenate the hypoxic tumor cells in addition to stimulating macrophage activity. It is preferred that the initial PFC emulsion administration be less than about 15 milliliters per kilogram of patient body weight as greater amounts tend to diminish the enhancement of macrophage activity. Again, it is preferred that subsequent administrations of PFC emulsion not exceed about 15 milliliters per kilogram of body weight per week.

Again, it is preferred that the chemotherapeutic agent be administered simultaneously with or more preferably as a mixture with the PFC emulsion. The radiation is preferably administered simultaneously with or immediately following administration of oxygen to the patient.

The following examples will further illustrate the nature and effect of the present invention.

EXAMPLE I

Fifty-one female $C_3HF$/Sed mice were treated with a lung colony assay to determine the number of artificial pulmonary metastasis developing in the lungs of normal and Fluosol-DA treated animals after intravenous injection of fibrosarcoma cells into a tail vein. Fluosol-DA was administered to 23 of the animals in an amount of about 15 milliliters per kilogram of animal body weight 7 days after the injection of fibrosarcoma cells. The Fluosol-DA treated animals were administered oxygen for a period of 30 minutes following the administration of Fluosol-DA. The animals were sacrificed 14 days after the injection of fibrosarcoma cells into the tail vein and fibrosarcoma tumor nodules were counted on the pleural surface of the lungs.

Tumor nodules were counted on twelve (52%) of the 23 Fluosol-DA treated mice. Twenty (71%) of the 28 untreated mouse had tumor nodules. The rate of spontaneous metastasis was reduced with Fluosol-DA treatment.

EXAMPLE II

B6D2F1/J male mice were given i.p. injections of 2 ml of a 2% starch solution. Two of the three groups were then injected with 0.3 ml of Fluosol-DA i.v. and were allowed to breath air or 95% oxygen (1 hr.). Macrophages were harvested 5 days later by washing their peritoneal cavities with phosphate buffered 0.9% saline containing heparin (10 units/ml). The macrophages were washed three times with phosphate buffered 0.9% saline and then suspended in MEM containing antibiotics, 10% fetal bovine serum and 15 mM HEPES ([4-(2-hydroxyethyl)-1-piperazineethanesulfonic acid]).

After determination by hemacytometer of viable (trypan blue exclusion) and differential cell counts, approximate numbers of macrophages were dispensed into the flat-bottomed wells of a culture plate. After incubation of 37° C. for 2 hrs., nonadherent macrophages were removed by washing 3-times with phosphate buffered 0.9% saline. These washings removed approximately 45–55% of the initially added cells. Then EMT6 cells ($5 \times 1^3$) were added to culture wells and the effector: target ratios, i.e., the ratio the number of macrophages to the number of tumor cells, were established on the basis of initial numbers of macrophages added to each well. The culture plates were incubated at 37° C. in 5% $CO_2$ for two days, then 0.5 uCi [$^3$H]thymidine was added to each well for 6 hrs. After washing, the harvested cells were lysed with 10% trichloroacetic acid, and the amount of [$^3$H]thymidine incorporated was determined in a liquid scintillation counter. The mean cpm were obtained from triplicate cultures, and the results were presented as percentage cytostasis which was calculated by the formula:

$$\% \text{ of cytostasis} = \frac{(A - B)}{A} \times 100$$

where A is cpm of cultures containing normal control macrophages, and B is cpm of cultures containing experimental macrophages.

FIG. 1 shows the cytoxicity of mice treated with Fluosol-DA and 1 hr. of carbogen breathing (○), Fluosol-DA and air (■), 1 hr. of carbogen breathing (●) and air breathing (□). Macrophages from mice receiving Fluosol-DA showed a profound cytotoxic effect at all effector:target ratios tested. Whether untreated animals breathed carbogen of air did not alter the cytostatic effect of the isolated macrophages; however, carbogen breathing had an enhancing effect on the cytostatic potential of macrophages isolated from Fluosol-DA treated mice.

EXAMPLE III

Lewis lung tumor was carried in C57BL/6J male mice. For the experiments $2 \times 10^6$ tumor cells prepared from a brei of several stock tumors were implanted subcutaneously in the legs of B6D2F1/J male mice 8 to 10 weeks of age. Treatment was initiated when the tumors were approximately 50 mm$^3$ in volume (about 1 week after tumor cell implantation).

Three groups of mice were injected with 5 mg I.p. carrageenan 24 hours prior to tumor cell implantation. There was no significant difference in tumor volume between normal tumor burdened mice and carrageenan pretreated mice bearing the Lewis lung tumor at the initiation of radiation treatment. Radiation was delivered in a single dose of 20 Gy with a Gamma Cell 40 (Atomic Energy of Canada; dose rate, 0.88 Gy per minute) to the tumor-bearing limb. The shielded portion of the animal received less than 2 percent of the delivered dose. The animals were anestesized with sodium pentobarbital (Abbott Laboratories, Chicago, IL) during the radiation treatment. The progress of each individual tumor was measured thrice weekly until it reached (or 60 days) a volume of 500 mm$^3$. Untreated Lewis lung tumor reach 500 mm$^3$ in about 14 days. Each treatment group had seven animals and each experiment was repeated twice, therefore each point represents the treatment outcome of 14 animals.

Fluosol-DA was administered on day 7 after tumor cell implantation, 95% $O_2$ breathing and x-ray treatment were administered immediately on day 0 or subsequent days.

Figure 2:
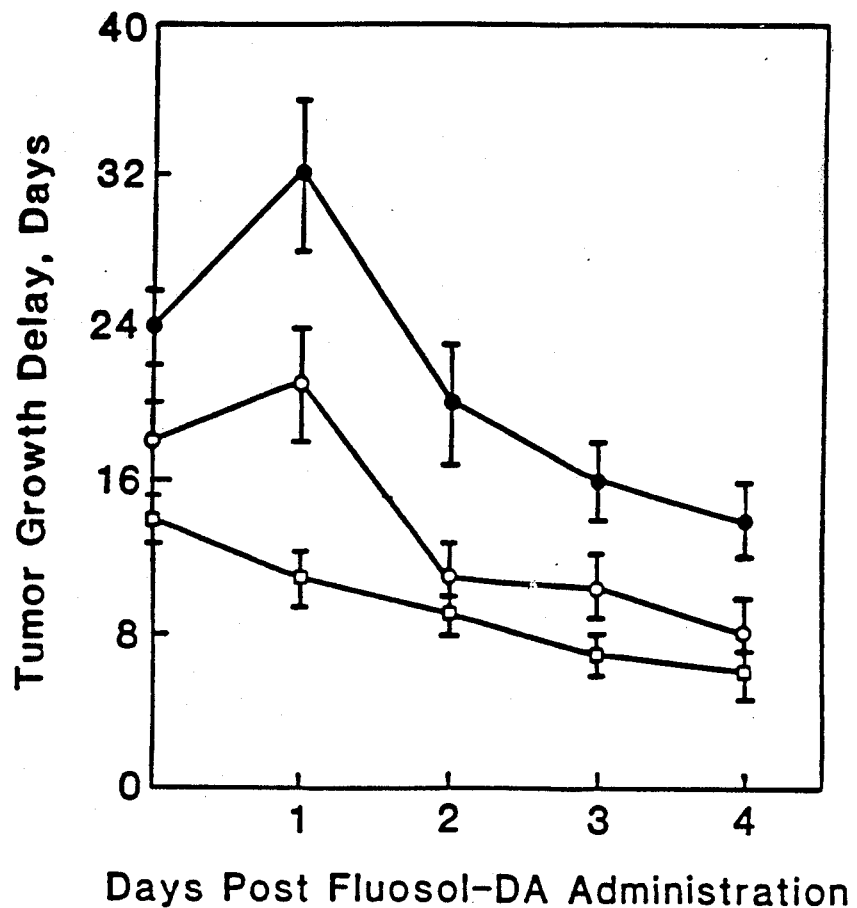
FIG. 2 is a graph showing the growth delay of Lewis lung tumor in animals produced by a single dose of radiation on animals treated with Fluosol with air breathing and pretreated with carrageenan as described in Example III.

FIG. 2. demonstrates the growth delay per tumor burdened animals following a single dose of X-rays of 20 Gy in animals treated with Fluosol-DA on day 0 and irradiated with air breathing on day 0, 1, 2, 3, or 4 (o). Results of animals treated with Fluosol-DA on day 0 and allowed to breath carbogen for 1 hr. prior to and during x-ray treatment on day 0, 1, 2, 3 or 4 (●) and in animals which breathed carbogen for 1 hour prior and during x-ray treatment on day 0, 1, 2, 3 or 4 (□) are also shown.

Figure 3:
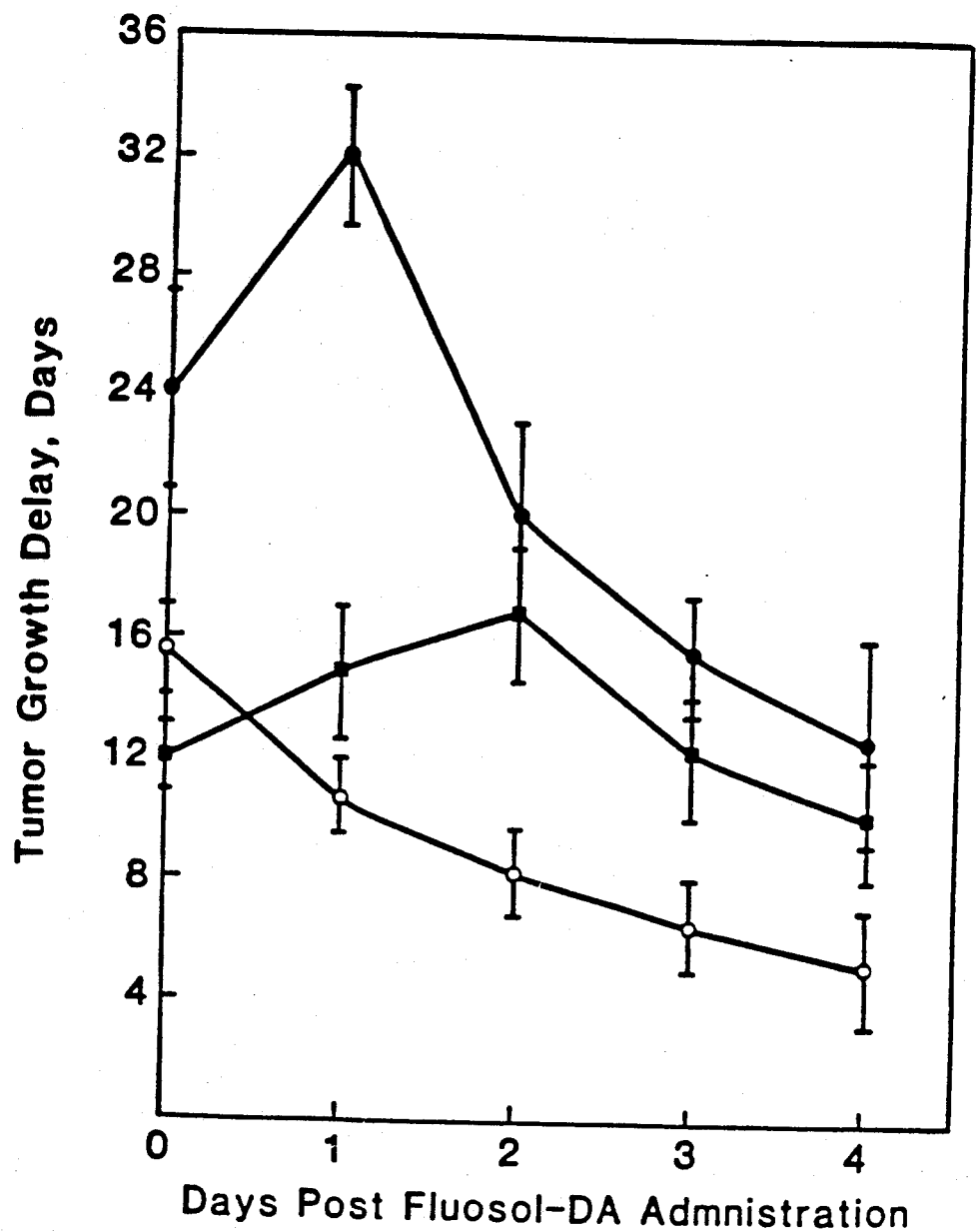
FIG. 3 is a graph showing the growth delay of Lewis lung tumors in animals produced by a single dose of radiation on animals treated with Fluosol and oxygen and pretreated with carrageenan as described in FIG. 3.

FIG. 3 indicates the growth delay obtained with the Lewis lung tumor produced by a single dose of x-rays of 20 Gy in animals pretreated with carrageenan and then treated with Fluosol-DA on day 0 and allowed to breath carbogen for 1 hour prior to and during x-ray treatment on day 0, 1, 2, 3 or 4 (●). Animal treated with Fluosol-DA on day 0, and allowed to breath carbogen for 1 hour prior to and during x-ray treatment on day 0, 1, 2, 3 or 4 (■) and animals which breathed carbogen for 1 hour prior to and during X-ray treatment on day 0, 1, 2, 3 or 4 (o) are also represented. Points are mean tumor growth delay, bars are S.E.M.

Administration of x-ray treatment and carbogen breathing 24 hours after Fluosol-DA injection resulted in an additional 8 days of tumor growth delay observed compared to x-ray treatment given immediately after Fluosol-DA injection (FIG. 2). In the treatment groups receiving Fluosol-DA with air breathing tumor growth delay was greater than in carbogen breathing animals 24 hours after Fluosol-DA administration and through the fourth day after x-ray treatments. In animals pretreated with carrageenan, and treated with x-rays and carbogen, the enhancement in tumor growth delay observed at 24 hrs. post Fluosol-DA administration is markedly diminished as is the tumor response observed at 2, 3 and 4 days post Fluosol-DA administration compared to animals without carrageenan. The difference of effects between tumor burdened animals pretreated with carrageenan (a macrophage poison) and non-pretreated animals represents the marked immunological stimulation exhibited by Fluosol-DA.

EXAMPLE IV

Lewis lung tumors were implanted subcutaneously in the hind limb of 324 mice. One hundred and eight of the animals were used as controls. Fluosol-DA was administered to 216 of the animals of from about 10 to about 15 milliliters of Fluosol-DA per kilogram of animal body weight. One hundred and eight of the Fluosol-DA treated animals were given oxygen (95%) for two hours on the day on which Fluosol-DA was administered. At day 25 or day 40, the animals were sacrificed and the pleural surface of the lungs examined to determine the number of metastases. The results are shown in Table I below.

TABLE I

| Group | Average Metastases per animal | |
|---|---|---|
| | Day 25 | Day 40 |
| Controls | 20 | all dead |
| Fluosol-room air | 5 | 32 |
| Fluosol-with oxygen | 5 | 15 |

Fluosol treated mice exposed to oxygen had significantly fewer metastases at day 40 than either the control animals or those treated with Fluosol but not exposed to oxygen.

EXAMPLE V

Mouse mammary tumors were implanted in the hind limbs of 56 mice. The mice were divided into seven groups of eight members per group. The groups are identified as follows:
  A. Control
  B. Fluosol only
  C. Radiation only D. Rad & O₂ 48 hrs Post Fluosol
E. Rad. & O₂ Immediately Post Fluosol
F. Rad. & O₂ 72 hrs Post Fluosol
G. Rad. &b O₂ 24 hrs Post Fluosol After seven days, Fluosol DA was administered to groups B, D, F and G in an amount of about 15 milliliters per kilogram of animal body weight. A single dose of radiation of about 2000 rads was administered to group C animals 7 days after implantation of the tumor. The same amount of radiation was administered to groups D-G. Groups D, F and G received oxygen and irradiation at intervals of 2, 3 and 1 days respectively, after the administration of Fluosol DA. Oxygen was administered to groups D, E, F and G one hour prior to radiation and during radiation.

Figure 4:
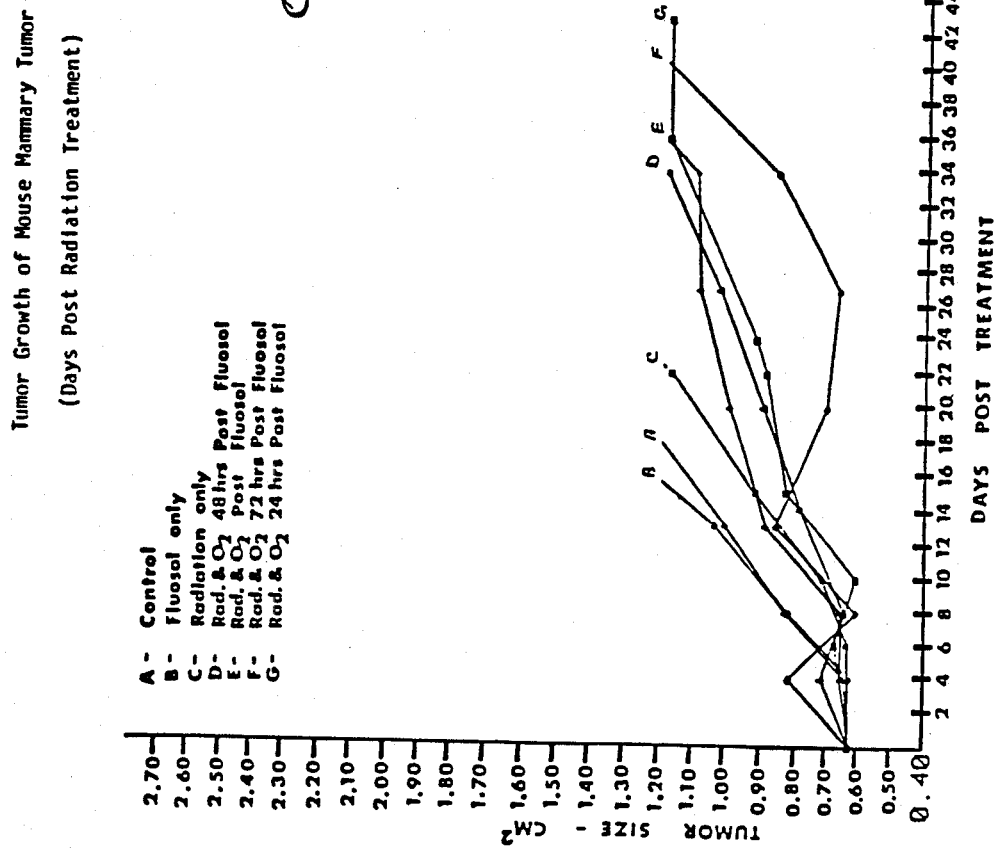
FIG. 4 is a graph showing Tumor Size vs. Days Past Radiation Treatment resulting from the experiments described in Example V herein.

The size of the tumor was measured by calipers at intervals post treatment. The results are charted in FIG. 4.

As can be seen, tumor growth is significantly delayed by treatment of radiation in combination with Fluosol and oxygen administration. It is believed that the majority of Fluosol-DA is removed from systemic circulation in mice within 24 hours post infusion. Therefore, the sensitization of hypoxic tumor cells to oxygenated systemic Fluosol would exhibit a growth delay effect only on day 0 and possibly day 1. The results observed and shown in FIG. 4 indicate a growth delay effect which is believed to be produced by activated macrophages affecting tumor necrosis following irradiation.

The preceding description has been presented with reference to the presently preferred embodiments of the invention. Workers skilled in the art and technology to which this invention pertains will appreciate that alterations and changes in the described methods and techniques can be practiced without meaningfully departing from the principles, spirit and scope of this invention. Accordingly, the foregoing description should not be read as pertaining only to the precise methods and techniques described, but rather should be read consistent with and as support for the following claims which are to have their fullest fair scope.

What is claimed is:

1. A method for reducing metastasis of a cancerous tumor in a patient comprising:
   a. administering to the patient an aqueous perfluorocarbon compound emulsion in an amount of from about 2 to about 15 milliliters per kilogram of body weight of the patient one or more times during a treatment period wherein the administration of perfluorocarbon compound emulsion does not exceed about 15 millilters per kilogram of body weight per week; and
   b. administering oxygen to the patient daily for at least about three days following each administration of the perfluorocarbon compound emulsion.

2. A method as claimed in claim 1 wherein the oxygen is administered as hyperbaric oxygen, high-inspired oxygen or carbogen and wherein each administration of oxygen lasts for a period of at least about 15 minutes.

3. A method as claimed in claim 2 wherein each administration of oxygen lasts for a period of from about 1 to about 4 hours.

4. A method as claimed in claim 1 wherein administration of perfluorocarbon compound emulsion provides a fluorocrit of from about 0.4% to about 3.0% when measured within about 1 hour of the administration of the perfluorocarbon compound emulsion.

5. A method as claimed in claim 1 wherein the perfluorocarbon compound emulsion is administered in an amount of from about 4 to about 10 milliliters per kilogram of body weight.

6. A method as claimed in claim 5 wherein the administration of perfluorocarbon compound emulsion provides a fluorocrit of from about 0.8% to about 2.0% when measured within 1 hour of the administration of the perfluorocarbon compound emulsion.

7. A method as claimed in claim 1 wherein perfluorochemical compound emulsion is administered one or more additional times at intervals of from about 3 days to about 21 days.

8. A method as claimed in claim 7 wherein the amount of perfluorocarbon compound emulsion administered after the initial administration of PFC emulsion does not exceed about 15 milliliters per kilogram of body weight per week.

9. A method as claimed in claim 8 wherein the amount of perfluorocarbon compound emulsion administered after the initial administration of PFC emulsion does not exceed about 10 milliliters per kilogram of body weight per week.

10. A method as claimed in claim 7 wherein oxygen is administered to the patient daily for at least about three days following each administration of perfluorochemical compound emulsion.

11. A method as claimed in claim 10 wherein oxygen is administered daily as hyperbaric oxygen, high-inspired oxygen or carbogen and wherein each oxygen administration lasts for a period of at least about 15 minutes.

12. A method as claimed in claim 11 wherein high-inspired oxygen is administered and wherein each oxygen administration lasts for a period from about 1 to about 4 hours.

13. A method as claimed in claim 1 further comprising administering a predetermined dosage of radiation to the patient at the location of the cancerous tumor during or immediately after the period in which oxygen is administered to the patient following administration of the perfluorocarbon compound emulsion.

14. A method as claimed in claim 13 wherein the perfluorochemical compound emulsion is administered in an amount of from about 6 to about 15 milliliters per kilogram of body weight.

15. A method as claimed in claim 1 further comprising administering a chemotherapeutic agent to the patient prior to, during or after the period in which oxygen is administered to the patient following administration of the perfluorocarbon compound emulsion.

16. A method for reducing metastasis of a cancerous tumor in a patient comprising:
   a. administrating to the patient an aqeuous perfluorocarbon compound emulsion at least twice during a treatment period at intervals of from about 3 to about 21 days during the treatment period, said perfluorocarbon compound emulsion being administered initially in an amount of from about 2 to about 15 milliliters per kilogram of body weight of the patient and administered in subsequent administrations in amounts which do not exceed about 15 milliliters per kilogram of body weight per week; and
   b. administering oxygen to the patient daily for a period of at least about three days following each administration of the perfluorocarbon compound emulsion.

17. A method as claimed in claim 16 wherein oxygen is administered to the patient daily during the treatment period.

18. A method as claimed in claim 16 wherein the perfluorocarbon compound emulsion is administered in subsequent administrations in amounts which do not exceed about 10 milliliters per kilogram as patient body weight.

19. A method as claimed in claim 16 wherein the oxygen is administered as hyperbaric oxygen, high-inspired oxygen or carbogen and wherein each administration lasts for a period of at least about 15 minutes.

20. A method as claimed in claim 16 wherein administration of perfluorocarbon compound emulsion provides a fluorocrit of from about 0.4% to about 3.0% when measured within 1 hour of the administration of the perfluorocarbon compound emulsion.

21. A method as claimed in claim 16 wherein the perfluorocarbon compound emulsion is administered intially in an amount of from about 4 to about 10 milliliters per kilogram of body weight.

22. A method as claimed in claim 16 further comprising administering a predetermined dosage of radiation to the patient at the location of the cancerous tumor during or immediately after the period in which oxygen is administered to the patient following administration of the perfluorocarbon compound emulsion.

23. A method as claimed in claim 22 wherein the radiation administration is fractionated and administered at predetermined intervals.

24. A method as claimed in claim 23 wherein the perfluorochemical compound emulsion is administered initially in an amount of from about 6 to about 15 milliliters per kilogram of body weight.

25. A method as claimed in claim 16 further comprising administering a chemotherapeutic agent to the patient priot to, during, or after the period in which oxygen is administered to the patient following administration of the perfluorocarbon compound emulsion.

26. A method as claimed in claim 25 wherein the chemotherapeutic agent is administered simultaneously with the administration of the perfluorocarbon compound emulsion.

27. A method for treating a cancerous tumor in a patient comprising:
   a. administering to the patient an aqueous perfluorocarbon compound emulsion one or more times during a treatment period at intervals of from about 3 to about 14 days, said perfluorocarbon compound emulsion being administered initially in an amount of from about 6 to about 15 milliliters of emulsion per kilogram of body weight of the patient and wherein subsequent administrations of perfluorocarbon compound emulsions do not exceed about 15 milliliters per kilogram of body weight per week;
   b. administering oxygen to the patient daily during the treatment period; and
   c. administering a predetermined dosage of radiation to the patient at the tumor location.

28. A method as claimed in claim 27 wherein the oxygen is administered daily as hyperbaric oxygen, high-inspired oxygen or carbogen, for a period of at least about 15 minutes.

29. A method as claimed in claim 28 wherein the oxygen is administered daily for a period of from about one to about four hours each day.

30. A method as claimed in claim 27 wherein the predetermined dosage of radiation administered is from about 1,000 to about 8,000 rads.

31. A method as claimed in claim 30 wherein the radiation administration is fractionated and administered at predetermined intervals.

32. A method as claimed in claim 31 wherein the radiation is administered at intervals of between about one and about ten times per week and the dosage of radiation administered at each interval is from about 100 to about 600 rads per day.

33. A method as claimed in claim 32 wherein the treatment period is from about two to about eight weeks.

34. A method as claimed in claim 31 wherein the radiation is administered in about five fractions per week for a period of about 6 to about 8 weeks, each fraction being from about 140 to about 240 rads.

35. A process for treating a cancerous tumor in a patient comprising:
   a. administering to the patient a perfluorocarbon compound emulsion one or more times during a treatment period at first predetermined intervals of from about 3 to about 21 days, said perfluorochemical compound emulsions being administered initially in an amount of from about 2 to about 15 milliliters per kilogram of body weight of the patient, and wherein subsequent administrations of perfluorocarbon compound emulsion do not exceed about 15 milliliters per kilogram of body weight per week;
   b. administering a chemotherapeutic agent to the patient one or more times during the treatment period at second predetermined intervals; and
   administering oxygen to the patient daily during the treatment period.

36. A process as claimed in claim 35 wherein the oxygen is administered as hyperbaric oxygen, high-inspired oxygen or carbogen and wherein each administration lasts for a period of at least about 15 minutes.

37. A process as claimed in claim 35 wherein the chemotherapeutic agent is mixed with perfluorocarbon compound emulsion and the chemotherapeutic agent is administered to the patient as a mixture with perfluorocarbon compound emulsion.

* * * * *